United States Patent
Dalko et al.

(10) Patent No.: US 6,846,812 B2
(45) Date of Patent: Jan. 25, 2005

(54) 7-OXO-DHEA COMPOUNDS FOR TREATING KERATINOUS CONDITIONS/AFFLICTIONS

(75) Inventors: Maria Dalko, Gif sur Yvette (FR); Alexandre Cavezza, Tremblay-en-France (FR); Elisabeth Picard-Lesboueyries, Velizy (FR); Béatrice Renault, Saint Maurice (FR); Véronique Burnier, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/170,679

(22) Filed: Jun. 14, 2002

(65) Prior Publication Data

US 2003/0054021 A1 Mar. 20, 2003

(30) Foreign Application Priority Data

Jun. 14, 2001 (FR) .............................................. 01 07804

(51) Int. Cl.$^7$ ............................................ A61K 31/566
(52) U.S. Cl. ...................................... 514/171; 514/178
(58) Field of Search ................................. 514/171, 178

(56) References Cited

U.S. PATENT DOCUMENTS

| | | | |
|---|---|---|---|
| 4,496,556 A | 1/1985 | Orentreich | |
| 5,424,463 A | 6/1995 | Lardy et al. | |
| 5,837,269 A | 11/1998 | Daynes et al. | |
| 5,843,932 A | 12/1998 | Labrie | |
| 6,399,084 B1 * | 6/2002 | Zenk et al. | ................. 514/177 |

FOREIGN PATENT DOCUMENTS

WO     WO 99/25333 A1     5/1999

OTHER PUBLICATIONS

Lardy et al., "Ergosteroids II: Biologically Active Metabolites and Synthetic Derivatives of Dehydroepiandrosterone", Steroids, Mar. 1998, vol. 63, No. 3, pps 158–165, Elsevier Science Publishers, New York, New York, USA.

French Search Report Dated Apr. 23, 2002 for FR 01/07804.

* cited by examiner

*Primary Examiner*—Barbara P. Badio
(74) *Attorney, Agent, or Firm*—Burns, Doane, Swecker & Mathis, L.L.P.

(57) ABSTRACT

7-Oxo-DHEA derivatives, various of which are themselves novel compounds, are well suited for cosmetically/therapeutically treating adverse conditions/afflictions of a keratinous substrate/material, notably of human skin, hair, eyelashes and nails, to improve the appearance thereof, in particular to prevent or treat signs of aging of the skin and/or a dull complexion and/or skin or hair pigmentation disorders and/or dryness of the skin and/or hyperseborrhoea and/or hyperseborrhoea-related imperfections and/or sensitive skin and/or dandruff and/or natural hair loss and/or baldness.

10 Claims, No Drawings

7-OXO-DHEA COMPOUNDS FOR TREATING KERATINOUS CONDITIONS/AFFLICTIONS

CROSS-REFERENCE TO PRIORITY APPLICATION

This application claims priority under 35 U.S.C. § 119 of FR-01/07804, filed Jun. 14, 2001, hereby expressly incorporated by reference.

BACKGROUND OF THE INVENTION

1. Technical Field of the Invention

The present invention relates to novel 7-oxo-DHEA derivatives, to a process for synthesizing such novel compounds and to cosmetic/therapeutic compositions comprising same.

The present invention also relates to cosmetic applications of at least one 7-oxo-DHEA derivative to improve the appearance of keratin materials and substrates, such as the skin, the hair, the eyelashes and the nails, in particular to prevent or treat adverse signs of aging of the skin and/or a dull complexion and/or skin or hair pigmentation disorders and/or dryness of the skin and/or hyperseborrhoea and/or hyperseborrhoea-related imperfections and/or sensitive skin and/or dandruff and/or natural hair loss and/or baldness.

This invention also relates to a cosmetic regime/regimen for treating keratinous substrates/materials by topical application thereon of a composition containing at least one 7-oxo-DHEA derivative, formulated into a physiologically acceptable medium therefor.

2. Description of the Prior Art

DHEA, or dehydroepiandrosterone, is a natural steroid produced essentially by the adrenal glands. Exogenous DHEA, administered topically or orally, is recognized for its capacity to promote epidermal keratinization (JP-07,196,467) and to treat dry skin by increasing the endogenous production and secretion of sebum and thus by reinforcing the skin's barrier effect (U.S. Pat. No. 4,496,556). U.S. Pat. No. 5,843,932 has also described the administration of DHEA to remedy dermal atrophy by inhibiting the loss of collagen and of connective tissue. Too, the assignee hereof has demonstrated the capacity of DHEA to combat the weathered appearance of the skin (FR-00/00349), to modify skin and hair pigmentation (FR-99/12773) and to combat epidermal atrophy (FR-00/06154). These properties of DHEA make it a candidate of choice as an anti-aging active agent.

However, DHEA has hormonal effects that may prove difficult as regards the administration of same. There need still exists to provide DHEA analogs with properties as advantageous as DHEA itself, but without eliciting any hormonal effects.

It was first considered by applicants that the 7-oxo-DHEA derivatives of general formula (I) below could satisfy this need:

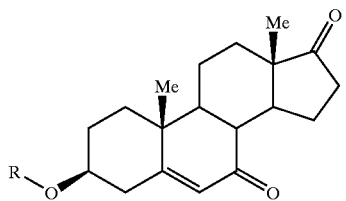
(I)

Among these compounds, 3β-acetoxy-7-oxo-DHEA or Δ5-androstene-3β-acetoxy-7,17-dione is already known and has been described as being effective in modulating the immune system (U.S. Pat. Nos. 5,292,730, 5,585,371 and 5,641,766), treating Alzheimer's disease (U.S. Pat. No. 5,707,983), treating HIV syndrome (U.S. Pat. No. 5,885,977) and for promoting weight loss (U.S. Pat. Nos. 5,296,481 and 5,807,848).

WO-99/25333 also indicates the administration, especially topically, of 3β-acetoxy-7-oxo-DHEA in the prophylactic and curative treatment of lupus erythematosus, which is a disorder of the immune system that is liable to affect several organs and that is manifested in the skin by transverse redness of the face and/or by squamous erythemal plaques disseminated over the body.

U.S. Pat. No. 5,424,463 especially describes 7-keto-DHEA (or Δ5-androstene-3β-ol-7,17-dione) and derivatives thereof wherein one or more of the hydroxyl or keto substituents is a group convertible thereto by hydrolysis. Hydrolyzable groups include hydroxyl groups esterified with an acid selected from the group consisting of (i) a normal, branched, saturated or unsaturated $C_2$–$C_{22}$ aliphatic acid, (ii) a $C_7$–$C_{22}$ aromatic acid, (iii) a $C_3$ or more dicarboxylic acid, for which only one carbonyl group is esterified with the 3-hydroxy group of the steroid, (iv) an inorganic acid such as sulfuric acid and phosphoric acid. U.S. Pat. No. 5,424,463 describes the 7-keto- and hydrolyzable derivatives thereof as being effective for promoting weight loss.

In addition, the following derivatives are also described as being effective for promoting weight loss (*Steroids*, 1998, 63(3), pp. 158–165): 3β-O-acetyl-7-oxo-dehydroepiandrosterone (or 3β-acetyl-7-oxo-DHEA);

3β-O-propionyl-7-oxo-dehydroepiandrosterone (or 3β-propionyl-7-oxo-DHEA);

3β-O-butanoyl-7-oxo-dehydroepiandrosterone (or 3β-butanoyl-7-oxo-DHEA);

3β-O-isobutanoyl-7-oxo-dehydroepiandrosterone;

3β-O-heptanoyl-7-oxo-dehydroepiandrosterone;

3β-O-dodecanoyl-7-oxo-dehydroepiandrosterone;

3β-O-palmitoyl-7-oxo-dehydroepiandrosterone;

3β-O-stearoyl-7-oxo-dehydroepiandrosterone;

3β-O-hemisuccinate-7-oxo-dehydroepiandrosterone.

Among the 7-oxo-DHEA derivatives of formula (I) that are described in the prior art are the following derivatives:

(1) The derivative of formula (I) in which R is a 2-tetrahydropyran group (RN 102 890-86-8).

(2) The compound of formula (I) in which R is a $CH_3OCO$ group, described as suppressing the transactivation of the androgenic receptor induced by an androstenediol in human prostate cancer cells (*Proc. Natl. Acad. Sci. USA*, 1999, 96(20), pp. 11173–11177).

(3) Derivatives of formula (I) in which R is an O=P(OH) $OCOCH_3$ group or a group

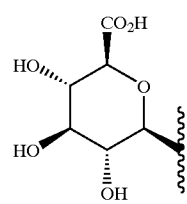

described in U.S. Pat. No. 5,837,269 as agents for increasing the immune response to a vaccine.

(4) The derivative of formula (I) in which R is a group mClPhCO, described in an epoxidation process for the synthesis of steroids (*J. Chem. Soc. Perkin Trans. I*, 1975 (4), pp. 323–6).

(5) Derivatives of formula (I) in which R is an NaSO₃H group or an SO₃H group, noted in *Endocrinol. Exp.*, 1971, 5(4), pp. 205–210, which describes the properties of these derivatives when they are subjected to various hydrolysis conditions.

(6) The derivative of formula (I) in which R is a tBuSi(Me)₂ group, described in a steroid preparation process (*Heterocycles*, 1994, 38(5), pp. 1053–60).

However, to the knowledge of applicants, it was heretofore unknown to administer the 7-oxo-DHEA derivatives of general formula (I) for cosmetic purposes, in particular for treating the adverse signs of aging.

SUMMARY OF THE INVENTION

The present invention thus features cosmetic applications for improving the appearance of keratinous substrates/materials, by administering to a candidate subject in need of such treatment, a thus-effective amount of at least one 7-oxo-DHEA compound of formula (I) below:

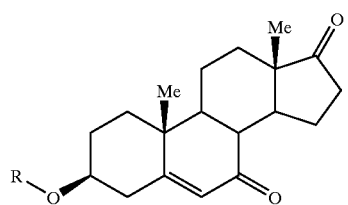

(I)

in which R is a saturated or unsaturated, linear or branched, or cyclic $C_1$–$C_{12}$ alkyl radical optionally containing one or more hetero atoms and optionally substituted with one or more substituents selected from among —OR' and/or —SR' and/or —COOR' and/or —NR'R' and/or halogen and/or sulfate and/or phosphate and/or aryl and/or heterocycle, said heterocycle advantageously being an indole, a pyrimidine, a piperidine, a morpholine, a pyran, a furan, a piperazine or a pyridine; an alkylcarbonyl radical, with the exception of the CH₃CO-radical, the $C_1$–$C_{24}$ alkyl moiety of which is saturated or unsaturated, linear or branched, or cyclic, and optionally substituted with one or more substituents selected from among —OR' and/or —SR' and/or —COOR' and/or —NR'R' and/or halogen and/or sulfate and/or phosphate and/or aryl and/or heterocycle, said heterocycle advantageously being an indole, a pyrimidine, a piperidine, a morpholine, a pyran, a furan, a piperazine or a pyridine; an arylcarbonyl radical, preferably a phenylcarbonyl radical, or an arylalkylcarbonyl radical, preferably a benzylcarbonyl radical, optionally substituted with one or more of the substituents —OR' and/or —SR' and/or COOR' and/or —NR'R' and/or halogen and/or aryl and/or heterocycle; a group O=P(OH)OR'; a group (O)₂SOR'; a trialkylsilyl radical (SiR'₃) in which the 3 groups R' may be identical or different; an alkyloxycarbonyl group (R'OCO); an alkylaminocarbonyl group (R'NHCO); wherein R' is a hydrogen atom, a saturated or unsaturated, linear or branched, or cyclic $C_1$–$C_{12}$ and preferably $C_1$–$C_6$ alkyl radical, which may optionally contain one or more hetero atoms, optionally functionalized with one or more of the groups —OR", —COOR", halogen, —NR"R", or with an aryl group, preferably a phenyl group, optionally functionalized with one or more of the groups —OR", —COOR", halogen or —NR"R", and preferably wherein R' is a hydrogen atom, a methyl, an ethyl, a butyl, a propyl or an isopropyl radical; and R" is a hydrogen atom or a saturated or unsaturated, linear or branched or cyclic alkyl radical, preferably $C_1$–$C_6$, preferably R" is a hydrogen atom, a methyl, an ethyl, a butyl, a propyl or an isopropyl radical; with the proviso that, in each of the groups —NR'R' and —NR"R", the substituents R' and R", respectively, are identical or different, and that, advantageously, the group —NR'R' represents an amino acid, preferably selected from among L-alanine, L-arginine, L-asparagine, L-aspartic acid, L-cysteine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine and L-valine.

DETAILED DESCRIPTION OF BEST MODE AND SPECIFIC/PREFERRED EMBODIMENTS OF THE INVENTION

More particularly according to the present invention, by "cyclic $C_1$–$C_{12}$ alkyl radical" is intended a cycloalkyl radical having from 3 to 12 carbon atoms.

The present invention also features the optical isomers and/or geometric isomers of the 7-oxo-DHEA derivatives of formula (I), either alone or in admixture in all proportions, and also the physiologically acceptable salts of these derivatives, said optical and/or geometric isomers deriving from the group R.

By the expression "keratin materials or substrates" is intended skin, hair fibers (head hair and eyelashes) and the nails.

According to one preferred embodiment of the invention, the 7-oxo-DHEA compounds of formula (I) are those in which R is a $C_1$–$C_6$, saturated or unsaturated, linear or branched, or cyclic alkyl radical optionally containing one or more hetero atoms, and optionally substituted with one or more substituents selected from among —OR' and/or —SR' and/or —COOR' and/or —NR'R' and/or halogen.

In another preferred embodiment of the invention, the 7-oxo-DHEA compounds of formula (I) are those in which R is an alkylcarbonyl radical, the $C_1$–$C_{20}$ and preferably $C_6$–$C_{18}$ alkyl moiety of which is saturated or unsaturated, linear or branched or cyclic and optionally substituted with one or more substituents selected from among —OR' and/or —SR' and/or —COOR' and/or —NR'R' and/or halogen.

Among the compounds of formula (I) according to the invention, the following are the most particularly preferred:

3β-O-methyl-7-oxo-dehydroepiandrosterone;
3β-O-ethyl-7-oxo-dehydroepiandrosterone;
3β-O-carboxymethyl-7-oxo-dehydroepiandrosterone;
3β-O-glucosyl-7-oxo-dehydroepiandrosterone;
3β-O-glucoronyl-7-oxo-dehydroepiandrosterone;
3β-O-(2-tetrahydropyranyl)-7-oxo-dehydroepiandrosterone;
3β-O-(2-tetrahydrofuranyl)-7-oxo-dehydroepiandrosterone;
3β-O-propionyl-7-oxo-dehydroepiandrosterone (or 3β-propionyloxy-7-oxo-DHEA);
3β-O-butanoyl-7-oxo-dehydroepiandrosterone (or 3β-butanoyloxy-7-oxo-DHEA);
3β-O-isobutanoyl-7-oxo-dehydroepiandrosterone;
3β-O-pentanoyl-7-oxo-dehydroepiandrosterone;
3β-O-hexanoyl-7-oxo-dehydroepiandrosterone;
3β-O-heptanoyl-7-oxo-dehydroepiandrosterone;

3β-O-octanoyl-7-oxo-dehydroepiandrosterone;
3β-O-nonanoyl-7-oxo-dehydroepiandrosterone;
3β-O-decanoyl-7-oxo-dehydroepiandrosterone;
3β-O-dodecanoyl-7-oxo-dehydroepiandrosterone;
3β-O-myristoyl-7-oxo-dehydroepiandrosterone;
3β-O-palmitoyl-7-oxo-dehydroepiandrosterone;
3β-O-stearoyl-7-oxo-dehydroepiandrosterone;
3β-O-arachidoyl-7-oxo-dehydroepiandrosterone;
3β-O-docosanoyl-7-oxo-dehydroepiandrosterone;
3β-O-lignoceroyl-7-oxo-dehydroepiandrosterone;
3β-O-oleoyl-7-oxo-dehydroepiandrosterone;
3β-O-linoleoyl-7-oxo-dehydroepiandrosterone;
3β-O-linolenoyl-7-oxo-dehydroepiandrosterone;
3β-O-petroselinoyl-7-oxo-dehydroepiandrosterone;
3β-O-7-oxo-dehydroepiandrosterone glycinate;
3β-O-7-oxo-dehydroepiandrosterone lysinate;
3β-O-7-oxo-dehydroepiandrosterone serinate;
3β-O-7-oxo-dehydroepiandrosterone α-glutamate;
3β-O-7-oxo-dehydroepiandrosterone α-aspartate;
3β-hemisuccinoyloxyandrost-5-ene-7,17-dione;
3β-O-(2-hydroxymalonyl)-7-oxo-dehydroepiandrosterone;
3β-O-(2-malonylaminocarbonyl)-7-oxo-dehydroepiandrosterone;
3β-O-(2-succinylaminocarbonyl)-7-oxo-dehydroepiandrosterone;
3β-O-(2-glutarylaminocarbonyl)-7-oxo-dehydroepiandrosterone;
3β-methylcarbonate-7-oxo-dehydroepiandrosterone;
3β-O-(trifluoroacetyl)-7-oxo-dehydroepiandrosterone;
3β-O-(4-carboxybutanoyl)-7-oxo-dehydroepiandrosterone;
3β-O-(4-cyclopentylbutanoyl)-7-oxo-dehydroepiandrosterone;
3β-O-benzoyl-7-oxo-dehydroepiandrosterone;
3β-O-(3,4-dihydroxybenzoyl)-7-oxo-dehydroepiandrosterone;
3β-O-(ascorbyl phosphate)-7-oxo-dehydroepiandrosterone;
3β-O-(ascorbyl sulfate)-7-oxo-dehydroepiandrosterone;
3β-O-phosphonyl-7-oxo-dehydroepiandrosterone;
3β-O-monoacetylphosphonyl-7-oxo-dehydroepiandrosterone;
3β-O-sulphonyl-7-oxo-dehydroepiandrosterone;
3β-O-(tert-butyldimethylsilyl)-7-oxo-dehydroepiandrosterone;
3β-O-(tert-butyldiphenylsilyl)-7-oxo-dehydroepiandrosterone;
3β-O-(trimethylsilyl)-7-oxo-dehydroepiandrosterone.

More particularly, the present invention also features the cosmetic administration of at least one 7-oxo-DHEA compound of formula (I) for preventing or treating the adverse signs of aging of the skin and/or a dull complexion and/or skin or hair pigmentation disorders and/or skin dryness and/or hyperseborrhoea and/or hyperseborrhoea-related imperfections and/or sensitive skin and/or dandruff and/or natural hair loss and/or baldness.

By the expression "signs of aging of the skin" are intended wrinkles and fine lines, loss of firmness and/or elasticity of the skin, cutaneous atrophy, a more irregular skin grain with presence of dilated pores, loss of radiance of the skin and/or pigmentary marks.

By the expression "sensitive skin" is intended skin that has been characterized in EP-0,680,749 B1, hereby incorporated by reference. It has thus been shown that the symptoms associated with sensitive skin included more or less painful sensations experienced in an area of skin, such as stinging, tingling, itching or pruritus, burning, redness, hotness, discomfort, tautness, etc. These symptoms may be manifested in response to various factors such as, inter alia, sweat, friction, the emotions, foods, the wind, shaving, soap, surfactants, hard water with a high calcium concentration, temperature variations or wool.

Thus invention also features cosmetic compositions containing, in a physiologically acceptable medium therefor (vehicle, diluent or carrier), at least one 7-oxo-DHEA derivative of formula (I) and at least one other active agent compound selected from among: a desquamating agent, a moisturizer, a depigmenting or propigmenting agent, an anti-glycation agent, an NO-synthase inhibitor, a 5α-reductase inhibitor, a lysyl and/or prolyl hydroxylase inhibitor, an agent for stimulating the synthesis of dermal or epidermal macromolecules and/or for preventing their degradation, an agent for stimulating the proliferation of fibroblasts and keratinocytes and/or keratinocyte differentiation, a muscle relaxant, a compound for reducing irritation, an antimicrobial agent, a tensioning agent, an anti-pollution agent or a free-radical scavenger.

The present invention also features cosmetic compositions containing, in a physiologically acceptable medium, at least one 7-oxo-DHEA compound of formula (I) and at least one UV-screening agent selected from among certain UVA and/or UVB screening agents and/or at least one optionally coated inorganic pigment.

The compositions according to the invention are well suited for topical application onto keratin substrates/materials such as the skin, keratin fibers (head hairs and eyelashes) and the nails.

By the expression "physiologically acceptable medium" is intended a medium that is compatible with the skin and/or its integuments.

To provide an order of magnitude, the compositions according to the invention advantageously contain from 0.00001% to 10% by weight of 7-oxo-DHEA derivative of formula (I) as defined above, relative to the total weight of the composition. Preferably, however, the subject compositions will contain from 0.001% to 5% by weight of 7-oxo-DHEA derivative of formula (I) relative to the total weight of the composition.

The above compositions are well suited for cosmetic purposes, to improve the appearance of keratin substrates/materials.

The subject compositions may thus be administered to prevent or treat the signs of aging of the skin and/or a dull complexion and/or skin or hair pigmentation disorders and/or skin dryness and/or hyperseborrhoea and/or hyperseborrhoea-related imperfections and/or sensitive skin and/or dandruff and/or natural hair loss and/or baldness.

Various compounds that may be formulated into the compositions according to the invention will now be more fully described.

1. Desquamating Agents and Moisturizers:
By the term "desquamating agent" is intended any compound capable of acting:
(a) either directly on desquamation by promoting exfoliation, such as β-hydroxy acids, in particular salicylic acid and derivatives thereof (including 5-n- octanoylsalicylic acid); α-hydroxy acids, such as glycolic acid, citric acid, lactic acid, tartaric acid, malic acid or mandelic acid; urea; gentisic acid; oligofucoses; cinnamic acid; extract of *Saphora japonica*; hydroxystilbenes including, in particular, resveratrol;

(b) or on the enzymes involved in the desquamation or degradation of corneodesmosomes, glycosidases, stratum corneum chymotryptic enzyme (SCCE), or even other proteases (trypsin, chymotrypsin-like). Exemplary agents for chelating mineral salts are EDTA; N-acyl-N,N',N'-ethylenediaminetriacetic acid; aminosulfonic compounds and in particular (N-2-hydroxyethylpiperazine-N-2-ethane)sulfonic acid (HEPES); 2-oxothiazolidine-4-carboxylic acid (procysteine); α-amino acid derivatives of the type such as glycine (as described in EP-0,852,949); honey; sugar derivatives such as O-octanoyl-6-D-maltose and N-acetylglucosamine.

By the term "moisturizer" is intended:

(a) either a compound acting on the barrier function, in order to maintain the moisturization of the stratum corneum, or an occlusive compound. Exemplary are the ceramides, sphingoid-based compounds, lecithins, glycosphingolipids, phospholipids, cholesterol and derivatives thereof, phytosterols (stigmasterol, β-sitosterol or campesterol), essential fatty acids, 1,2-diacylglycerol, 4-chromanone, pentacyclic triterpenes, petroleum jelly and lanolin;

(b) or a compound that directly increases the water content of the stratum corneum, such as threalose and derivatives thereof, hyaluronic acid and derivatives thereof, glycerol, pentanediol, pidolates, serine, xylitol, sodium lactate, polyglyceryl acrylate, ectoin and derivatives thereof, chitosan, oligosaccharides and polysaccharides, cyclic carbonates, N-lauroyl-pyrrolidonecarboxylic acid and N-α-benzoyl-L-arginine;

(c) or a compound that activates the sebaceous glands, such as steroid derivatives (including DHEA) and vitamin D and derivatives thereof.

These compounds advantageously constitute from 0.001% to 30% and preferably from 0.01% to 20% of the total weight of the composition according to the invention.

The compositions according to the present invention comprising the desquamating agents and moisturizers indicated above are well suited for preventing or treating skin dryness and especially xerosis.

2. Depigmenting or Propigmenting Agents:

Exemplary depigmenting agents that may be formulated into the compositions according to the present invention comprise the following compounds: kojic acid; ellagic acid; arbutin and derivatives thereof such as those described in EP-895,779 and EP-524,109; hydroquinone; aminophenol derivatives such as those described in WO-99/10318 and WO-99/32077, and in particular N-cholesteryloxycarbonyl-para-aminophenol and N-ethyloxycarbonyl-para-aminophenol; iminophenol derivatives, in particular those described in WO-99/22707; L-2-oxothiazolidine-4-carboxylic acid or procysteine, and also its salts and esters; ascorbic acid and derivatives thereof, especially ascorbyl glucoside; and plant extracts, in particular extracts of liquorice, of mulberry and of skullcap, this list not intended to be limiting.

Propigmenting agents that are exemplary include the extract of burnet (*Sanguisorba officinalis*) marketed by Maruzen, and extracts of chrysanthemum (*Chrysanthemum morifolium*).

The compositions according to the present invention comprising the depigmenting agents indicated above are well suited for preventing or treating hyperpigmentation, in particular pigmentary marks related to aging of the skin.

The compositions containing the propigmenting agents indicated above are well suited for treating baldness.

3. Anti-glycation Agents:

By the term "anti-glycation agent" in intended a compound for preventing and/or reducing the glycation of skin proteins, in particular of dermal proteins such as collagen.

Exemplary anti-glycation agents are plant extracts of the *Ericacea* family, such as an extract of blueberry (*Vaccinium angustifolium*); ertothioneine and derivatives thereof; and hydroxystilbenes and derivatives thereof, such as resveratrol and 3,3',5,5'-tetrahydroxystilbene. These anti-glycation agents are described in FR-99/16166, FR-00/08158, FR-99/09267 and FR-99/16168, respectively. Resveratrol is particularly preferred for formulation into the compositions of the invention.

The compositions of the invention comprising an anti-glycation agent as defined above are well suited to prevent or treat the signs of aging of the skin, in particular to prevent or treat the loss of tonicity and/or elasticity of the skin.

4. NO-synthase Inhibitors:

Exemplary NO-synthase inhibitors that are suitable for formulation into the compositions of the present invention especially comprise a plant extract of the species *Vitis vinifera* which is marketed by Euromed as Leucocyanidines de raisins extra, or by Indena under the trademark Leucoselect®, or also by Hansen as Extrait de marc de raisin; a plant extract of the species *Olea europaea* which is preferably obtained from olive tree leaves and is marketed by Vinyals in the form of a dry extract, or by Biologia & Technologia under the trademark Eurol BT; and a plant extract of the species *Gingko biloba* which is preferably a dry aqueous extract of this plant marketed by Beaufour as *Gingko biloba* extrait standard.

The compositions according to the invention comprising an NO-synthase inhibitor as defined above are well suited to prevent or treat the signs of aging of the skin and/or sensitive skin.

5. 5α-reductase Inhibitors:

When the compositions according to the invention comprise a 5α-reductase inhibitor, such inhibitor is advantageously selected from among:

retinoids, and in particular retinol;

sulfur and sulfur derivatives;

zinc salts such as zinc lactate, gluconate, pidolate, carboxylate, salicylate and/or cysteate;

selenium chloride;

vitamin B6 or pyridoxine;

mixture of capryl250 glycine, sarcosine and extract of *Cinnamomum zeylanicum* marketed by Seppic under the trademark Sepicontrol A5®;

an extract of *Laminaria saccharina* marketed by SECMA under the trademark Phlorogine®;

an extract of *Spiraea ulmaria* marketed by Silab under the trademark Sebonormine®;

plant extracts from the species *Arnica montana, Cinchona succirubra, Eugenia caryophyllata, Humulus lupulus, Hypericum perforatum, Mentha piperita, Rosmarinus officinalis, Salvia oficinalis* and *Thymus vulgaris*, all marketed, for example, by Maruzen;

an extract of *Serenoa repens* marketed by Euromed;

plant extracts of the genus *Silybum*;

plant extracts containing sapogenins and in particular extracts of diosgenin-rich or hecogenin-rich *Dioscorea* plants; and extracts of *Eugenia caryophyllata* containing eugenol or eugenyl glucoside.

The 5α-reductase inhibitor advantageously constitutes, for example, from 0.001% to 10% and preferably from 0.01% to 5% of the total weight of the composition according to the invention. When this composition contains such a compound, it is particularly suitable for preventing or treating seborrhoea and/or hirsutism and/or androgen-dependent alopecia.

6. Lysyl and/or Prolyl Hydroxylase Inhibitors:

Preferred examples of lysyl and/or propyl hydroxylase inhibitors that may be formulated into the compositions according to the present invention are 2,4-diaminopyrimidine 3-oxide or 2,4-DPO described in WO-96/09048 and 2,4-diamino-6-piperidinopyrimidine 3-oxide or "Minoxidil" described in U.S. Pat. Nos. 4,139,619 and 4,596,812.

These compounds are advantageously present, for example, in the compositions of the invention in a proportion of from 0.001% to 5% by weight and preferably in a proportion of from 0.01% to 5% by weight relative to the total weight of the composition.

The compositions containing the lysyl and/or prolyl hydroxylase inhibitor and the 7-oxo-DHEA derivative of formula (I) are advantageously used for treating alopecia.

7. Agents for Stimulating the Synthesis of Dermal or Epidermal Macromolecules and/or for Preventing Their Degradation:

Among the active agents for stimulating dermal macromolecules, exemplary are those that act:

(a) either on collagen synthesis, such as extracts of *Centella asiatica*; asiaticosides and derivatives thereof; ascorbic acid or vitamin C and derivatives thereof; synthetic peptides such as lamin, biopeptide CL or the palmitoyloligopeptide marketed by Sederma; peptides extracted from plants, such as the soybean hydrolysate marketed by Coletica under the trademark Phytokine®; plant hormones such as auxins and cinnamic acid and derivatives thereof, as described in the European patent application published under No. 0,925,779;

(b) or on elastin synthesis, such as the extract of *Saccharomyces cerivisiae* marketed by LSN under the trademark Cytovitin®; and the extract of the alga *Macrocystis pyrifera* marketed by SECMA under the trademark Kelpadelie®;

(c) or on glycosaminoglycan synthesis, such as the product of fermentation of milk with *Lactobacillus vulgaris*, marketed by Brooks under the trademark Biomin yogourth®; the extract of the brown alga *Padina pavonica* marketed by Alban Müller under the trademark HSP3®; and the extract of *Saccharomyces cerevisiae* available from Silab under the trademark Firmalift® or from LSN under the trademark Cytovitin®;

(d) or on fibronectin synthesis, such as the extract of the zooplankton Salina marketed by Seporga under the trademark GP4G®; the yeast extract available from Alban Müller under the trademark Drieline®; and the palmitoyl pentapeptide marketed by Sederma under the trademark Matrixil®;

(e) or on metalloprotease (MMP) inhibition, such as, more particularly, MMP 1, 2, 3 or 9: exemplary are the retinoids and derivatives, isoflavonoids, oligopeptides and lipopeptides, lipoamino acids, the malt extract marketed by Coletica under the trademark Collalift®; extracts of blueberry or of rosemary; carotenoids including, in particular, lycopene; isoflavones, their derivatives or plant extracts containing them, in particular extracts of soybean (marketed, for example, by Ichimaru Pharcos under the trademark Flavosterone SB®), of red clover, of flax, of kakkon, of sage or extracts of sage (as described in French patent application No. 00/10203);

(f) or on the inhibition of serine proteases such as leukocyte elastase or cathepsin G: exemplary are the peptide extract of Leguminosa seeds (*Pisum sativum*) marketed by LSN under the trademark Parelastyl®, and heparinoids and pseudodipeptides.

Among the active agents that stimulate epidermal macromolecules, such as fillagrin and keratins, especially representative are the extract of lupin marketed by Silab under the trademark Structurine®; the extract of beech *Fagus sylvatica* buds marketed by Gattefosse under the trademark Gatuline®, and the extract of the zooplankton Salina marketed by Seporga under the trademark GP4G®.

The compositions according to the invention containing one or more of the above compounds are particularly suitable for preventing or treating the signs of aging of the skin, in particular loss of firmness and/or elasticity of the skin.

8. Agents for Stimulating the Proliferation of Fibroblasts or Keratinocytes and/or Keratinocyte Differentiation:

Exemplary agents for stimulating the proliferation of fibroblasts that may be formulated into the compositions of the invention include plant proteins or polypeptides, extracts, especially of soybean (for example an extract of soybean marketed by LSN under the trademark Eleseryl SH-VEG 8® or marketed by Silab under the trademark Raffermine®); and plant hormones such as giberrellins and cytokinins.

The agents for stimulating keratinocyte proliferation that may be formulated into the compositions according to the invention especially comprise retinoids such as retinol and its esters, including retinyl palmitate; extracts of nut cakes marketed by Gattefosse; and extracts of *Solanum tuberosum* marketed by Sederma.

The agents for stimulating keratinocyte differentiation comprise, for example, minerals such as calcium; the extract of lupin marketed by Silab under the trademark Photopreventine®; sodium beta-sitosteryl sulfate marketed by Seporga under the trademark Phytocohesine®; and the extract of corn marketed by Solabia under the trademark Phytovityl®.

The compositions according to the invention comprising these compounds are preferably used for preventing or treating the signs of aging of the skin.

9. Muscle Relaxants:

The muscle relaxants that may be included in the compositions according to the invention comprise calcium inhibitors such as alverine and its salts, chlorine-channel openers such as diazepam, and catecholamine and acetylcholine inhibitors, such as the hexapeptide argireline R marketed by Ilipotec.

The compositions of the invention comprising these compounds are used for preventing or treating the signs of aging of the skin and in particular wrinkles.

10. Antimicrobial Agents:

Exemplary antimicrobial agents that may be formulated into the compositions according to the invention include 2,4,4'-trichloro-2'-hydroxydiphenyl ether (or triclosan), 3,4,4'-trichloro-banilide, phenoxyethanol, phenoxypropanol, phenoxy-isopropanol, hexamidine isethionate, metronidazole and its salts, micronazole and its salts, itraconazole, terconazole, econazole, ketoconazole, saperconazole, fluconazole, clotrimazole, butoconazole, oxiconazole, sulphaconazole, sulconazole, terbinafine, ciclopirox, ciclopiroxolamine, undecylenic acid and its salts, benzoyl peroxide, 3-hydroxybenzoic acid, 4-hydroxy-benzoic acid, phytic acid, N-acetyl-L-cysteine acid, lipoic acid, azelaic acid and its salts, arachidonic acid, resorcinol, 2,4,4'-trichloro-2'-hydroxydiphenyl ether, 3,4,4'-trichlorocarbanalide, octopirox, octoxyglycerine, octanoylglycine, caprylyl glycol, 10-hydroxy-2-decanoic acid, dichlorophenylimidazole dioxolane and its derivatives described in WO-93/18743, farnesol and phytosphingosines, and mixtures thereof.

The preferred antimicrobial agents are triclosan, phenoxyethanol, octoxyglycerine, octanoyl-glycine, 10-hydroxy-2-decanoic acid, caprylyl glycol, farnesol and azelaic acid.

By way of example, the antimicrobial agents may be formulated into the compositions of the invention in amounts advantageously representing from 0.1% to 20% and preferably from 0.1% to 10% of the total weight of the composition.

The compositions containing the 7-oxo-DHEA derivative of formula (I) and the antimicrobial agent are particularly suitable for treating acne-prone greasy skin, acne or dandruff of the scalp.

11. Tensioning Agents:

By the term "tensioning agent" is intended a compound capable of exerting tension on the skin, the effect of which is to temporarily fade out irregularities on the skin's surface, such as wrinkles and fine lines.

Among the tensioning agents that may be formulated into the compositions of the present invention, especially representative are:
  (1) polyurethane latices or acrylic-silicone latices, in particular those described in EP-1,038,519, such as a propylthio(polymethylacrylate), propylthio (polymethyl methacrylate) or propylthio (polymethacrylic acid) grafted polydimethyl-siloxane, or alternatively a propylthio(polyisobutyl methacrylate) and propylthio(polymethacrylic acid) grafted polydimethylsiloxane. Such grafted silicone polymers are marketed by 3M under the trademark VS 80, VS 70 or LO21.
  (2) soybean or wheat plant proteins, and/or
  (3) sodium magnesium silicates (Laponites).

The compositions according to the invention comprising the above tensioning agents are well suited for treating the signs of aging of the skin, in particular wrinkles and fine lines.

12. Anti-pollution Agents or Free-radical Scavengers:

By the term "anti-pollution agent" is intended any compound capable of trapping ozone, monocyclic or polycyclic aromatic compounds such as benzopyrene and/or heavy metals such as cobalt, mercury, cadmium and/or nickel. By the term "free-radical scavenger" is intended any compound capable of trapping free radicals.

Exemplary ozone-trapping agents that may be formulated into the compositions according to the invention are, in particular, vitamin C and derivatives thereof, including ascorbyl glucoside; phenols and polyphenols, in particular tannins, ellagic acid and tannic acid; epigallocatechin and natural extracts containing same; extracts of olive tree leaf; extracts of tea, in particular of green tea; anthocyans; extracts of rosemary; phenol acids, in particular chlorogenic acid; stilbenes, in particular resveratrol; sulfur-containing amino acid derivatives, in particular S-carboxymethylcysteine; ergothioneine; N-acetylcysteine; chelating agents, for instance N,N'-bis(3,4,5-trimethoxybenzyl)ethylenediamine or one of its salts, metal complexes or esters; carotenoids such as crocetin; and various starting materials, for instance the mixture of arginine, histidine ribonucleate, mannitol, adenosine triphosphate, pyridoxine, phenyl-alanine, tyrosine and hydrolysed RNA, marketed by Laboratoires Sérobiologiques under the trademark CPP LS 2633-12F®, the water-soluble fraction of corn marketed by Solabia under the trademark Phytovityl®, the mixture of extract of fumitory and of extract of lemon marketed under the trademark Unicotrozon C-49® by Induchem, and the mixture of extracts of ginseng, of apple, of peach, of wheat and of barley, marketed by Provital under the trademark Pronalen Bioprotect®.

Exemplary agents for trapping out monocyclic or polycyclic aromatic compounds according to the invention are, in particular, tannins such as ellagic acid; indole derivatives, in particular 3-indolecarbinol; extracts of tea, in particular of green tea, extracts of water hyacinth or *Eichhornia crassipes*; and the water-soluble fraction of corn marketed by Solabia under the trademark Phytovityl®.

Finally, exemplary heavy-metal-trapping agents that may be formulated into the compositions according to the invention include, in particular, chelating agents such as EDTA, the pentasodium salt of ethylenediamine tetramethylenephosphonic acid, and N,N'-bis(3,4,5-trimethoxybenzyl) ethylenediamine or one of the salts, metal complexes or esters thereof; phytic acid; chitosan derivatives; extracts of tea, in particular of green tea; tannins such as ellagic acid; sulfur-containing amino acids such as cysteine; extracts of water hyacinth (*Eichhornia crassipes*); and the water-soluble fraction of corn marketed by Solabia under the trademark Phytovityl®.

The free-radical scavengers that may be included in the compositions according to the invention comprise, other than certain anti-pollution agents indicated above, vitamin E and derivatives thereof such as tocopheryl acetate; bioflavonoids; coenzyme Q10 or ubiquinone; certain enzymes, for example, catalase, superoxide dismutase, lactoperoxidase, glutathione peroxidase and quinone reductases; glutathione; benzylidenecamphor; benzylcyclanones; substituted napthalenones; pidolates; phytanetriol; gamma-oryzanol; lignans; and melatonin.

The compositions of the invention comprising the anti-pollution agents and/or free-radical scavengers indicated above are well suited for preventing or treating the signs of aging of the skin, in particular wrinkles, and loss of firmness and elasticity of the skin and dehydration. As a variant, same are useful for preventing or treating a dull complexion.

13. UVA and/or UVB Screening Agents and Optionally Coated Inorganic Pigments:

The compositions according to the invention may contain one or more UV-screening agents capable of screening out UVA and/or UVB radiation.

Exemplary compounds for screening out UVA radiation include, especially:
  (1) benzophenone derivatives, for example:
    2,4-dihydroxybenzophenone (benzophenone-1);
    2,2',4,4'-tetrahydroxybenzophenone (benzo-phenone-2);
    2-hydroxy-4-methoxybenzophenone (benzo-phenone-3), available from BASF under the trademark Uvinul M40;

2-hydroxy-4-methoxybenzophenone-5-sulfonic acid (benzophenone-4) and also its sulfonate form (benzophenone-5), available from BASF under the trademark Uvinul MS40;

2,2'-dihydroxy-4,4'-dimethoxybenzophenone (benzophenone-6);

5-chloro-2-hydroxybenzophenone (benzophenone-7);

2,2'-dihydroxy-4-methoxybenzophenone (benzophenone-8);

the disodium salt of 2,2'-dihydroxy-4,4'-dimethoxybenzophenone-5,5'-disulfonic acid (benzophenone-9);

2-hydroxy-4-methoxy-4'-methylbenzophenone (benzophenone-10);

benzophenone-11;

2-hydroxy-4-(octyloxy)benzophenone (benzophenone-12);

benzophenones 3 and 5 being preferred;

(2) triazine derivatives, and in particular 2,4-bis{[4-(2-ethylhexyloxy)-2-hydroxy]phenyl}-6-(4-methoxyphenyl)-1,3,5-triazine available from Ciba Geigy under the trademark Tinosorb S and 2,2'-methylenebis[6-(2H-benzotriazol-2-yl)-4-(1,1,3,3-tetramethylbutyl)phenol] available from Ciba Geigy under the trademark Tinosorb M;

(3) benzene-1,4-bis(3-methylidene-10-camphorsulfonic acid), optionally in partially or totally neutralized form, and (4) mixtures thereof.

Exemplary compounds for screening out UVB radiation include:

(1) salicylic acid derivatives, in particular homomenthyl salicylate and octyl salicylate;

(2) cinnamic acid derivatives, in particular 2-ethylhexyl p-methoxycinnamate, available from Givaudan under the trademark Parsol MCX;

(3) liquid β,β'-diphenylacrylate derivatives, in particular 2-ethylhexyl α-cyano-α,β'-diphenylacrylate, or octocrylene, available from BASF under the trademark Uvinul N539;

(4) p-aminobenzoic acid derivatives;

(5) 4-methylbenzylidenecamphor available from Merck under the trademark Eusolex 6300;

(6) 2-phenylbenzimidazole-5-sulfonic acid marketed under the trademark "Eusolex 232" by Merck;

(7) 1,3,5-triazine derivatives, in particular:
2,4,6-tris[p-(2'-ethylhexyl-1'-oxycarbonyl)anilino]-1,3,5-triazine, available from BASF under the trademark Uvinul T150, and
the compound having the formula (A) below:

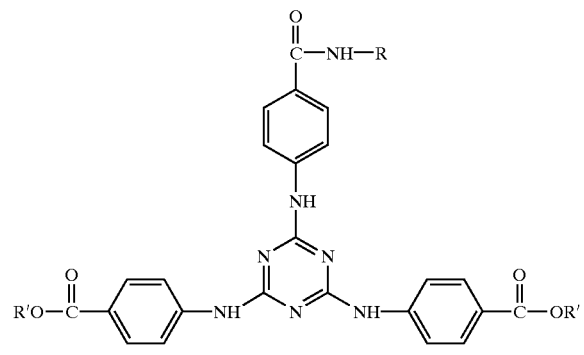

(A)

in which R' is a 2-ethylhexyl radical and R is a tert-butyl radical, available from Sigma 3V under the trademark Uvasorb HEB;

(8) mixtures thereof.

Exemplary compounds for screening out UVA and UVB radiation are, in particular:

(1) plant extracts, in particular of rosemary (rosmarinic acid) and of the genus *Leontopodium*, in particular a plant species *Leontopodium alpinum* or *Leontopodium stracheyi*;

(2) the benzotriazole silicone having the general formula (B) below:

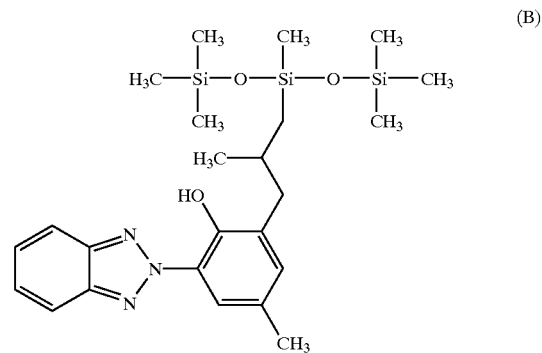

(B)

This benzotriazole silicone, and also the method for preparing it, are especially described in FR-A-2,642,968.

Exemplary optionally coated inorganic pigments include nanopigments of titanium dioxide, of iron oxide, of zinc oxide, of zirconium oxide or of cerium oxide optionally coated with alumina and/or with aluminum stearate.

14. Compounds of Neurogenic Origin for Reducing Irritation:

Exemplary compounds of neurogenic origin for reducing irritation include:

(1) substance P antagonists and in particular those described in EP-0,680,749, extracts of at least one non-photosynthetic filamentous bacterium, particularly strains of *Vitreoscilla filiformis* described in EP-0,761,204, the spring waters described in EP-0,764,440, extracts of at least one plant of the Rosacea family, particularly of the species *Rosa gallica* described in the European patent application published under No. 0,906,752 and the alkaline earth metals described in the European patent applications published under Nos. 0,737,471 and 0,770,302;

(2) CGRP antagonists, in particular those described in EP-0,765,668 and especially Iridacea extracts, particularly of the species *Iris pallida*;

(3) NO-synthase inhibitors;

(4) bradykinin antagonists and in particular those described in the European patent application published under No. 0,909,556;

(5) cytokine antagonists;

(6) histamine antagonists;

(7) antagonists of interleukin 1 and/or of tumor necrosis factor of α type (TNFα) and in particular those described in the European patent applications published under Nos. 0,892,642 and 0,764,444, particularly peptide Modulene, the tripeptide Lysine-Proline-Valine (KPV) and an extract of at least one plant from the Labiae family, particularly of the species *Rosmarinus officinalis*;

(8) sodium-channel blockers preferably selected from among: Amiloride, Quinidine, Quinidine sulfate, Apamine, Cyproheptadine, Loperamide and N-acetylprocainamide (9) potassium-channel openers, especially Minoxidil and derivatives thereof.

In addition to the compound(s) described above, the compositions according to the invention generally contain an effective amount of 7-oxo-DHEA derivatives of formula (I) as defined above, that is sufficient to elicit the desired effect. It thus contains, for example, from 0.00001% to 10% by weight of the 7-oxo-DHEA derivative of formula (I), relative to the total weight of the composition, and preferably from 0.001% to 5% by weight of the 7-oxo-DHEA derivative of formula (I) relative to the total weight of the composition.

This invention also features novel 7-oxo-DHEA derivatives of formula (I) that may be formulated into cosmetics and that are readily synthetically available, especially by carrying out one of the processes more fully described hereinbelow.

Thus, the present invention features novel 7-oxo-DHEA compounds of general formula (I) described above, comprising:

a group O=P(OH)OR' with the exception of the O=P(OH)$_2$ group and the O=P(OH)OCOCH$_3$ group;

a group (O)$_2$SOR' with the exception of the Na.SO$_3$H group and the SO$_3$H group;

a trialkylsilyl group (SiR'$_3$) in which the 3 groups R' may be identical or different, with the exception of the tBu Si(Me)$_2$ group;

an alkyloxycarbonyl group (R'OCO) with the exception of the CH$_3$OCO group;

an alkylaminocarbonyl group (R'NHCO) wherein the alkyl moiety is necessarily substituted with one or more of the groups —OR' and/or —SR' and/or —COOR' and/or —NR'R' and/or halogen and/or sulfate and/or phosphate and/or glycoside and/or aryl and/or heterocycle, such heterocycle preferably being an indole, a pyrimidine, a piperidine, a morpholine, a pyran, a furan, a piperazine, or a pyridine;

in which R'R", —NR'R' and —NR"R" have the same definitions as described above; and compounds of formula (I) selected from among:

3β-O-pentanoyl-7-oxo-dehydroepiandrosterone;

3β-O-hexanoyl-7-oxo-dehydroepiandrosterone;

3β-O-octanoyl-7-oxo-dehydroepiandrosterone;

3β-O-nonanoyl-7-oxo-dehydroepiandrosterone;

3β-O-decanoyl-7-oxo-dehydroepiandrosterone;

3β-O-myristoyl-7-oxo-dehydroepiandrosterone;

3β-O-arachidoyl-7-oxo-dehydroepiandrosterone;

3β-O-docosanoyl-7-oxo-dehydroepiandrosterone;

3β-O-lignoceroyl-7-oxo-dehydroepiandrosterone;

3β-O-oleoyl-7-oxo-dehydroepiandrosterone;

3β-O-linoleoyl-7-oxo-dehydroepiandrosterone;

3β-O-linolenoyl-7-oxo-dehydroepiandrosterone;

3β-O-petroselinoyl-7-oxo-dehydroepiandrosterone;

3β-O-methyl-7-oxo-dehydroepiandrosterone;

3β-O-ethyl-7-oxo-dehydroepiandrosterone;

3β-O-carboxymethyl-7-oxo-dehydroepiandrosterone;

3β-O-glucosyl-7-oxo-dehydroepiandrosterone;

3β-O-(2-tetrahydrofuranyl)-7-oxo-dehydroepiandrosterone;

3β-O-(trifluoroacetyl)-7-oxo-dehydroepiandrosterone;

3β-O-(4-cyclopentylbutanoyl)-7-oxo-dehydroepiandrosterone;

3β-O-(3,4-dihydroxybenzoyl)-7-oxo-dehydroepiandrosterone.

Among the novel derivatives of formula (I), the following compounds are most particularly preferred:

3β-O-7-oxo-dehydroepiandrosterone glycinate;

3β-O-7-oxo-dehydroepiandrosterone lysinate;

3β-O-7-oxo-dehydroepiandrosterone serinate;

3β-O-7-oxo-dehydroepiandrosterone α-glutamate;

3β-O-7-oxo-dehydroepiandrosterone α-aspartate;

3β-O-(2-hydroxymalonyl)-7-oxo-dehydroepiandrosterone;

3β-O-(2-malonylaminocarbonyl)-7-oxo-dehydroepiandrosterone;

3β-O-(2-succinylaminocarbonyl)-7-oxo-dehydroepiandrosterone;

3β-O-(2-glutarylaminocarbonyl)-7-oxo-dehydroepiandrosterone;

3β-O-(ascorbyl phosphate)-7-oxo-dehydroepiandrosterone;

3β-O-(ascorbyl sulphate)-7-oxo-dehydroepiandrosterone;

3β-O-(t-butyldiphenylsilyl)-7-oxo-dehydroepiandrosterone;

3β-O-(trimethylsilyl)-7-oxo-dehydroepiandrosterone.

This invention also features compositions comprising, in a physiologically acceptable medium, at least one novel 7-oxo-DHEA derivative as defined above.

Too, the compositions according to the invention may comprise the novel 7-oxo-DHEA compounds as described above either alone or as mixtures in all proportions.

The amount of novel 7-oxo-DHEA derivatives as described above that may be formulated into the compositions according to the invention obviously depends on the desired effect and must be in an effective amount that is sufficient to obtain or elicit the desired effect.

To provide an order of magnitude, the compositions of the invention advantageously contain at least one novel 7-oxo-DHEA derivative as described above in an amount representing from 0.00001% to 10% of the total weight of the composition and preferably in an amount representing from 0.001% to 5% of the total weight of the composition.

The novel DHEA compounds are readily synthesized: said compounds are prepared in one step from 7-oxo-DHEA, especially via various synthetic methods that will be more fully described hereinbelow.

The 7-oxo-DHEA, which constitutes one of the starting materials used in said synthetic methods, is itself obtained in two steps from 3β-O-acetyl-DHEA.

The first step is an oxidation reaction in the allylic position of 3β-O-acetyl-DHEA according to a technique described, for example, in *Tetrahedron Letters*, 1997, 38, 119–122, which permits obtaining 3β-O-acetyl-7-oxo-DHEA.

The second step is a deprotection reaction which prepares 7-oxo-DHEA from the 3β-O-acetyl-7-oxo-DHEA obtained in the preceding step by a transesterification reaction, which essentially entails dissolving the 3β-O-acetyl-7-oxo-DHEA in an alcoholic solvent, adding an alkali metal alkoxide, stirring the reaction medium and then, after reaction, processing the reaction medium under conditions conventionally employed in organic chemistry, the residue obtained being recrystallized or purified on a column of silica.

According to the invention, by the expression "inert atmosphere" is intended argon or nitrogen and by the expression "room temperature" is intended a temperature ranging from between 15° to 25° C.

The purification techniques that may optionally be employed at the end of each of the steps of the processes according to the invention are performed according to standard methodology of organic synthesis.

The novel 7-keto-DHEA compounds described above are obtained in one step from 7-oxo-DHEA according to various synthetic methods that will now be more fully described.

According to one preferred embodiment of the invention, a first general method for synthesizing the novel 3β-O-alkylcarbonyl-7-oxo-DHEA derivatives entails placing 7-oxo-DHEA in a polar aprotic solvent and then adding an organic base and an acid chloride thereto. After reaction and processing the reaction medium under conditions conventionally employed in organic chemistry, the residue obtained is then crystallized or purified on a column of silica.

The acid chlorides not commercially available may be prepared via standard methods of organic chemistry.

According to another preferred embodiment of the invention, a second general method for synthesizing the novel 3β-O-alkylcarbonyl-7-oxo-DHEA compounds entails adding a carbonyldiimidazole dissolved in a polar aprotic solvent to carboxylic acid dissolved in the same solvent, and then, to the solution stirred without heating, adding 7-oxo-DHEA dissolved in the same solvent, stirring the mixture under cold conditions and then at room temperature overnight and then, after reaction, processing the reaction medium under conditions conventionally employed in organic chemistry, and the residue is then purified by chromatography or by recrystallization.

According to another preferred embodiment of the invention, a general method for synthesizing the novel 3β-O-alkyl-7-oxo-DHEA derivatives entails placing 7-oxo-DHEA in a polar aprotic solvent and then adding an alkali metal hydride under cold conditions, stirring the reaction medium and then, after adding an alkyl halide, maintaining the reaction medium at room temperature, and, after reaction, processing the reaction medium under conditions conventionally employed in organic chemistry, and the residue obtained is then recrystallized or purified on a column of silica.

According to yet another preferred embodiment of the invention, a general method for synthesizing the 7-keto-DHEA carbamates entails placing 7-oxo-DHEA in an anhydrous aprotic solvent, heating the reaction medium after addition, under inert atmosphere, of an isocyanate and an organic base, and, after reaction, processing the reaction medium under conditions conventionally employed in organic chemistry, and the residue obtained is then recrystallized or purified by chromatography.

Specific examples of the preparation of the novel 7-oxo-DHEA compounds according to the invention are set forth in the examples to follow.

The compositions according to the invention are well suited for cosmetic or pharmaceutical applications, particularly dermatological use. Preferably, the compositions of the invention are well suited for cosmetic applications.

The compositions according to the invention may be administered for cosmetic purposes, to improve the appearance of keratin materials, in particular to prevent or treat the adverse signs of aging of the skin and/or a dull complexion and/or skin or hair pigmentation disorders and/or skin dryness and/or hyperseborrhoea and/or hyperseborrhoea-related imperfections and/or sensitive skin and/or dandruff and/or natural hair loss and/or baldness.

The compositions according to the invention are preferably formulated for topical application to keratin materials such as the skin, the hair, the eyelashes or the nails. They may be in any presentation form normally used for this type of application, especially in the form of an aqueous or oily solution, an oil-in-water or water-in-oil emulsion, a silicone emulsion, a microemulsion or nanoemulsion, an aqueous or oily gel or a liquid, pasty or solid anhydrous product.

The subject compositions may be more or less fluid and may have the appearance of a white or colored cream, an ointment, a milk, a lotion, a serum, a paste, a mousse or a gel. They may optionally be topically applied onto the skin in the form of an aerosol, a patch or a powder. They may also be in solid form, for example, in the form of a stick. They may be used as care products and/or as makeup products for the skin. Alternatively, they may be formulated as shampoos or conditioners.

In known fashion, the compositions of the invention may also contain additives and adjuvants that are common in cosmetics, such as hydrophilic or lipophilic gelling agents, preservatives, antioxidants, solvents, fragrances, fillers, pigments, odor absorbers and dyestuffs. The amounts of these various additives and adjuvants are those conventionally employed in the field under consideration, and range, for example, from 0.01% to 20% of the total weight of the composition. Depending on their nature, these additives and adjuvants may be introduced into the fatty phase or into the aqueous phase. These additives and adjuvants, and the concentrations thereof, must be such that they do not adversely affect the advantageous properties of the 7-oxo-DHEA derivatives of formula (I) according to the invention.

When the composition according to the invention is an emulsion, the proportion of the fatty phase advantageously ranges from 2% to 80% by weight and preferably from 5% to 50% by weight relative to the total weight of the composition. The fatty substances, emulsifiers and co-emulsifiers included in the composition in emulsion form are selected from among those conventionally formulated in the field under consideration. The emulsifier and co-emulsifier are preferably present in the composition in a proportion ranging from 0.3% to 30% by weight and preferably from 0.5% to 20% by weight relative to the total weight of the composition.

Exemplary fatty substances according to the invention include the oils and especially mineral oils (liquid petroleum jelly), oils of plant origin (avocado oil, soybean oil), oils of animal origin (lanolin), synthetic oils (perhydrosqualene), silicone oils (cyclomethicone) and fluoro oils (perfluoro polyethers). Fatty alcohols such as cetyl alcohol, fatty acids, waxes and gums and in particular silicone gums are also representative fatty substances.

Exemplary emulsifiers and co-emulsifiers according to the invention include fatty acid esters of polyethylene glycol, such as PEG-100 stearate, PEG-50 stearate and PEG-40 stearate; fatty acid esters of polyols, such as glyceryl stearate, sorbitan tristearate and oxyethylenated sorbitan stearates commercially available under the trademark Tween® 20 or Tween® 60, for example; and mixtures thereof.

And exemplary hydrophilic gelling agents include in particular, carboxyvinyl polymers (carbomer), acrylic copolymers such as acrylate/alkyl acrylate copolymers, polyacrylamides, polysaccharides, natural gums and clays. Exemplary lipophilic gelling agents include, in particular, modified clays, for example bentones, metal salts of fatty acids and hydrophobic silica.

The present invention also features a cosmetic regime/regimen for treating keratin substrates by topical application thereon of a composition containing, formulated into a physiologically acceptable medium (vehicle, diluent or carrier), at least one 7-oxo-DHEA derivative having the above formula (I), either alone or in combination with at least one other compound as described above.

This invention relates more particularly to a cosmetic regime or regimen for treating the adverse signs of aging of the skin and/or a dull complexion and/or skin or hair pigmentation disorders and/or skin dryness and/or hyperseborrhoea and/or hyperseborrhoea-related imperfections and/or sensitive skin and/or dandruff and/or natural hair loss and/or baldness, comprising the topical application onto the skin or the hair, for such period of time as required to elicit the desired cosmetic/therapeutic response, of a composition containing, formulated into a physiologically acceptable medium, at least one 7-oxo-DHEA derivative having the above formula (I), either alone or in combination with at least one other compound as described above.

Each citation indicated above, whether of the open literature, patent, patent application, or otherwise, is hereby expressly incorporated by reference.

In order to further illustrate the present invention and the advantages thereof, the following specific examples are given, it being understood that same are intended only as illustrative and in nowise limitative.

In said examples to follow, all parts and percentages are given by weight.

EXAMPLE 1

This example describes a variety of specific compositions according to the invention.

| Composition 1; Moisturizing Cream: | | |
|---|---|---|
| Phase A: | | |
| Acrylate/$C_{10-30}$ acrylate copolymer | | 0.5% |
| Water | | 12.0% |
| Phase B: | | |
| Hydrogenated polyisobutene | | 5.0% |
| 3β-O-7-oxo-DHEA α-glutamate | | 0.5% |
| Cyclohexasiloxane | | 6.0% |
| Phase C: | | |
| Triethanolamine | | 1.0% |
| Glycerol | | 6.0% |
| EDTA | | 0.2% |
| Preservatives | | 0.5% |
| Glycine | | 2.0% |
| Polyacrylamide and $C_{13-14}$ isoparaffin and laureth-7 | | 1.0% |
| Water | qs | 100% |

This composition was prepared in the following manner. The polymer of phase A was dispersed in water at 40° C. The constituents of phase B were heated to 70° C. until completely dissolved, and the temperature was then reduced to 40° C. The constituents of phase C were mixed together at 50° C. Phase B was then introduced into phase A at 40° C. with stirring, and phase C was then added thereto.

The above composition rehydrates dry skin and renders it smooth.

| Composition 2; Moisturizing Cream: | | |
|---|---|---|
| The composition below was formulated in conventional manner. | | |
| Phase A: | | |
| Demineralized water | qs | 100% |
| Preservatives | | 0.5% |
| Carbomer | | 0.4% |
| Glycerol | | 7.0% |
| Phase B1: | | |
| Oxyethylenated (200 EO) sorbitan stearate | | 0.9% |
| Phase B2: | | |
| PEG-100 stearate and glyceryl stearate | | 2.1% |
| Isononyl isononanoate | | 10.0% |
| Petroleum jelly | | 2.0% |
| Octyldodecanol | | 10.0% |
| 3β-O-sulfonyl-7-oxo-DHEA | | 0.2% |
| Butylhydroxytoluene | | 0.1% |
| UV-screening agent | | 1.0% |
| Ceramides | | 0.5% |
| Phase C: | | |
| Water | | 2.0% |
| Triethanolamine | | 0.5% |
| Urea | | 1.0% |
| This cream is useful for caring for dry skin. | | |

| Composition 3; Anti-Aging Cream: | | |
|---|---|---|
| Phase A: | | |
| Acrylate/$C_{10-30}$ acrylate copolymer | | 0.5% |
| Water | | 12.0% |
| Phase B: | | |
| Isononyl isononanoate | | 5.0% |
| 3β-O-(2-Malonylaminocarbonyl)-7-oxo-DHEA | | 0.5% |
| Cyclohexasiloxane | | 5.0% |
| Octyl methoxycinnamate | | 1.0% |
| Phase C: | | |
| Triethanolamine | | 1.0% |
| Glycerol | | 6.0% |
| Preservatives | | 0.5% |
| Polyacrylamide and C13–14 isoparaffin and laureth-7 | | 1.0% |
| Water | qs | 100% |

This composition was prepared in the following manner. The polymer of phase A was dispersed in water at 40° C. The constituents of phase B were heated to 70° C. until completely dissolved, and the temperature was then reduced to 40° C. The constituents of phase C were mixed together at 50° C. Phase B was then introduced into phase A at 40° C. with stirring, and phase C was then added thereto.

This cream is advantageously topically applied once or twice a day for treating the signs of aging of the skin, and in particular for reducing or fading out wrinkles and fine lines.

| Composition 4; Anti-Aging Cream: | | |
|---|---|---|
| The composition below was formulated in conventional manner. | | |
| Phase A: | | |
| Demineralized water | qs | 100.0% |
| Preservatives | | 0.5% |
| Carbomer | | 0.4% |
| Glycerol | | 7.0% |
| Phase B1: | | |
| Oxyethylenated (200 EO) sorbitan stearate | | 0.9% |
| Phase B2: | | |
| PEG-100 stearate and glyceryl stearate | | 2.1% |
| Isononyl isononanoate | | 10.0% |
| Octyldecanol | | 10.0% |

-continued

| | |
|---|---|
| 3β-O-Butanoyl-7-oxo-DHEA | 0.2% |
| Butylhydroxytoluene | 0.1% |
| UV-screening agent | 1.0% |
| Phase C: | |
| Water | 2.0% |
| Triethanolamine | 0.5% |
| Extract of *Centella asiatica* | 1.0% |
| Palmitoyl pentapeptide (Matrixyl ® marketed by Sederma) | 0.1% |

This cream is useful as a firming day cream.

Composition 5; Gel For Cleansing Greasy Skin:

The following composition was formulated in conventional manner.

| | |
|---|---|
| Lauryl phosphate | 6.50% |
| Decyl glucoside | 16.25% |
| Polyquaternium-7 | 5.70% |
| Oxyethylenated (150 EO) pentaerythrityl tetrastearate | 0.50% |
| Glycerol | 3.50% |
| Sorbitol | 3.50% |
| Potassium hydroxide | 1.70% |
| Hydroxypropylcellulose | 0.20% |
| Disodium EDTA | 0.05% |
| Sodium chloride | 0.10% |
| 3β-O-heptanoyl-7-oxo-DHEA | 0.10% |
| Preservatives | 0.30% |
| Water | qs 100% |

This gel is useful to control the secretions of sebum and to attenuate skin imperfections.

Composition 6: Anti-Blemish Patch:

A patch comprising the composition below was assembled:

| | |
|---|---|
| Water | 40.0% |
| Alcohol | qs |
| Glycerol | 7.0% |
| 3β-O-(ascorbyl sulfate)-7-oxo-DHEA | 0.5% |
| Polyvinyl alcohol | 5.0% |
| Kojic acid | 0.5% |

This patch may be applied to the hands and the neckline to fade out pigmentary marks, in particular age marks.

Composition 7; Lotion For Preventing Hair Loss:

The composition below was formulated in conventional manner.

| | |
|---|---|
| Water | 25.0% |
| Glycerol | 7.0% |
| 3β-O-Stearoyl-7-oxo-DHEA | 0.5% |
| Alcohol | qs 100% |

This lotion is effective for preventing natural hair loss.

EXAMPLE 2

Synthesis of 3β-O-acetyl-7-oxo-DHEA

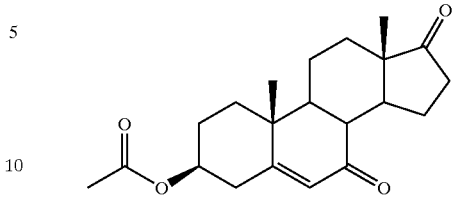

A solution of 10 g of 3β-O-acetyl-DHEA in 200 ml of acetonitrile was prepared. 60 mg of copper iodide (CuI) were added thereto under an inert atmosphere. The solution was cooled to between 5° and 10° C. and 19.6 ml of 80% t-BuOOH were added dropwise. At the end of the addition, the reaction medium was allowed to return to room temperature and was stirred for 2 hours, followed by heating at 50° C. for 20 hours. The reaction medium was then cooled and poured into 300 g of 10% sodium bicarbonate (NaHCO$_3$) solution. This mixture was extracted three times with diethyl ether and the organic solution was then washed with saturated NaHCO$_3$ solution, and then with saturated sodium chloride (NaCl) solution. After drying and evaporating to dryness, the crude product was obtained in the form of a solid. The residue was recrystallized from an acetone/hexane mixture.

(a) Melting point: 190–192° C.;
(b) Yield: 91%;
(c) $[\alpha]_d = -76°$ (methanol);
(d) $^1$H NMR and mass spectrometry in agreement.

EXAMPLE 3

Synthesis of 7-oxo-DHEA

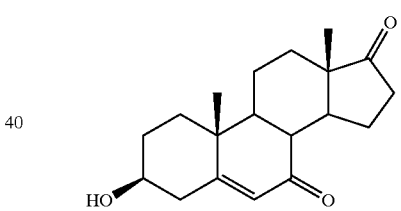

A solution of 3β-O-acetyl-7-oxo-DHEA obtained in Example 2 in methanol was prepared. 1 molar equivalent of sodium methoxide (NaOMe) was added and the mixture was stirred for a period of between 3 and 12 hours. The methanol was evaporated off and the residue was diluted with water and extracted with dichloromethane. The organic solution was dried and then evaporated to dryness. The residue was purified by chromatography to give the 7-oxo-DHEA.

EXAMPLE 4

Synthesis of 3β-O-linoleoyl-7-oxo-DHEA

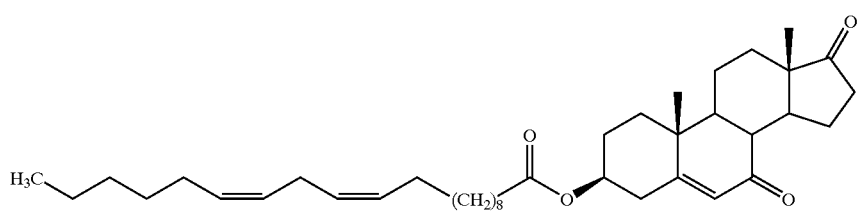

1 equivalent of 7-oxo-DHEA obtained in Example 3 was dissolved in 70 ml of dichloromethane in a reactor. 1.5 equivalents of triethylamine and 1.25 equivalents of linoleic acid chloride were then added. The mixture was reacted at room temperature for 20 hours. The medium was then diluted with dichloromethane, washed with saturated NaHCO₃ solution and then washed a second time with water. The organic phase was dried over sodium sulfate, filtered and concentrated to dryness under vacuum. The residue obtained was recrystallized or purified on a column of silica.

EXAMPLE 5

Synthesis of 3β-O-methyl-7-oxo-DHEA

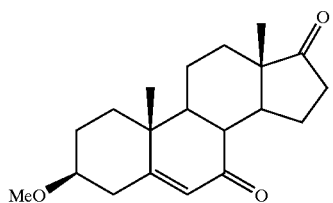

1 equivalent of 7-oxo-DHEA obtained in Example 3 was dissolved in 70 ml of dimethylformamide in a reactor. 1.2 equivalents of sodium hydride (60% in oil) was then added at 0° C. and the mixture was stirred for half an hour. 1.5 equivalents of methyl iodide were then added and the mixture was reacted at room temperature for 20 hours. The medium was then diluted with diethyl ether, washed with saturated NaHCO₃ solution and then washed a second time with water. The organic phase was dried over sodium sulphate, filtered and concentrated to dryness under vacuum. The residue obtained was recrystallized or purified on a column of silica.

EXAMPLE 6

Synthesis of 3β-O-7-oxo-DHEA α-glutamate

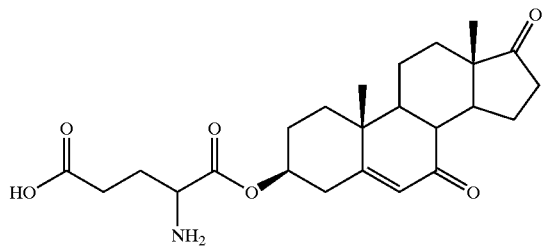

A solution of 0.5 mmol of 5-tert-butyl N-tert-butoxycarbonyl-L-glutamate was prepared in 2 ml of dichloromethane at 0° C. 0.5 mmol of carbonyldiimidazole dissolved in 2 ml of dichloromethane was added. The solution was stirred at 0° C. for 20 minutes, followed by addition of 0.45 mmol of 7-oxo-DHEA (obtained in Example 3) dissolved in 2 ml of dichloromethane. The mixture was stirred at 0° C. for 1 hour and then at room temperature for 15 hours. The reaction medium was evaporated to dryness and then taken up in 5 ml of ethyl acetate. The solution was washed with 5 ml of saturated aqueous NaCl solution, then with 5 ml of 1N sulfuric acid, then with 5 ml of water, then with 5 ml of saturated aqueous sodium bicarbonate solution and then with 5 ml of water. The residual organic phase was dried over sodium sulfate and then evaporated to dryness. The residue was purified by chromatography on a column of silica to give the protected expected product.

Deprotection was carried out by treatment with 2 ml of a dichloromethane/trifluoroacetic acid mixture (1:1 ratio) for 30 minutes at room temperature. The mixture was then evaporated to dryness to give 3β-O-7-oxo-DHEA α-glutamate.

EXAMPLE 7

Synthesis of 3β-O-(2-glutarylaminocarbonyl)-7-oxo-DHEA

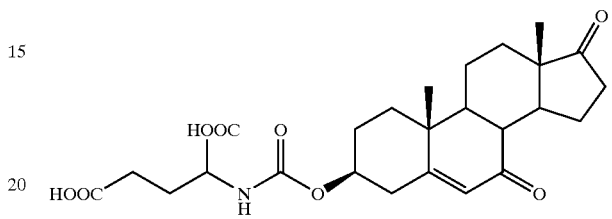

A solution of 7-oxo-DHEA obtained in Example 3 in an anhydrous aprotic solvent, for example anhydrous toluene (benzene) or anhydrous THF, was prepared. 1 molar equivalent of 2-isocyanate ester of succinic acid and 2 molar equivalents of pyridine were added under an inert atmosphere. The solution was heated at 80° C. (or in refluxing THF, 70° C.) for 1–12 hours. The reaction medium was evaporated to dryness and the residue was then taken up in a solvent, for instance ethyl acetate or dichloromethane. After several acidic, basic and neutral washes, the organic solution was dried and then evaporated to dryness. The residue was purified by chromatography or by recrystallization to give the protected expected product.

Deprotection was carried out by treatment with a mixture of dichloromethane/trifluoroacetic acid (in a 1:1 ratio) for 30 minutes at room temperature. The mixture was then evaporated to dryness to give 3β-O-(2-glutarylaminocarbonyl)-7-oxo-DHEA.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for cosmetically/therapeutically treating an adverse condition/affliction of a keratinous substrate/material to improve the apperance thereof, comprising topically applying onto such keratinous substrate/material, an appearance-enhancing effective amount of at least one 7-oxo-DHEA compound having the structural formula (I):

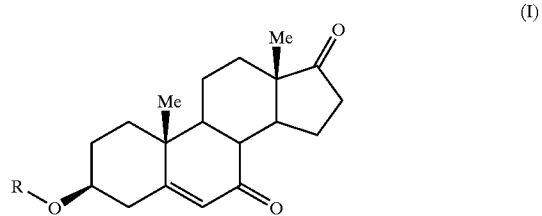

in which R is an alkylcarbonyl radical wherein the alkyl is a $C_1$–$C_{24}$ alkyl moiety which is saturated or unsaturated, linear or branched, or cyclic and is subsituted with —COOR' and/or —NR'R';

wherein R' is a hydrogen atom or a saturated or unsaturated, linear or branched, or cyclic $C_1$–$C_{12}$ alkyl radical, the alkyl radical optionally containing one or more hetero atoms and optionally being functionalized with one or more of the groups —OR", —COOR", halogen, —NR"R", or with an aryl group, the aryl group optionally being functionalized with one or more of the groups —OR", —COOR", halogen or —NR"R"; and R" is a hydrogen atom or a saturated or unsaturated, linear or branched or cyclic alkyl radical;

with the proviso that, in each of the groups —NR'R' and —NR"R", the substituents R' and R", respectively, are identical or different;

wherein the adverse condition/afflication of a keratinous substrate/material is hyperseborrhea and/or imperfections associated thereto, and/or dandruff and/or natural hair loss and/or baldness.

2. The method as defined by claim 1, wherein formula (I), each of the groups R' and R" is a hydrogen atom or a $C_1$–$C_6$ alkyl radical.

3. The method as defined by claim 1, wherein formula (I), each of the groups R' and R" is a hydrogen atom, or a methyl, ethyl, butyl, propyl or isopropyl radical.

4. The method as defined by claim 1, comprising topically co-applying onto such keratinous substrate/material, an effective amount of at least one other active agent compound selected from the group consisting of desquamating agents, moisturizes, depigmenting or propigmenting agents, antiglycation agents, NO-synthase inhibitors, 5α-reductase inhibitors, lysyl and/or prolyl hydoxylase inhibitors, agents for stimulating the synthesis of dermal or epidermal macromolecules or for preventing their degradation, agents for stimulating the proliferation of fibroblasts and keratinocytes and/or keratinocyte differentiation, muscle relaxants, compounds for reducing irritation of neurogenic origin, antimicrobial agents, tensioning agents, anti-pollution agents, and free-radical scavengers.

5. The method as defined by claim 1, comprising topically co-applying onto such keratinous substrate/material, an effective amount of at least one optionally coated inorganic pigment and/or at least one UV-screening agent selected from the group consisting of:

(a) a benzophenone derivative;
(b) a triazine derivative;
(c) benzene-1,4-bis(3-methylidene-10-camphorsulfonic acid), optionally in partially or totally neutralized state;
(d) a salicylic acid derivative;
(e) a cinnamic acid derivative;
(f) a liquid β, β'-diphenylarcrylate derivative;
(g) a p-aminobenzoic acid derivative;
(h) 4-methylbenzylidenecamphor;
(i) 2-phenylbenzimidazole-5-sulfonic acid;
(j) a 1,3,5-triazine derivative;
(k) a plant extract which comprises an extract of *Rosmarinus officinalis, Leontopodium alpinum* and/or *Leontopodium stracheyi*; and
(l) a benzotriazole silcone having the formula:

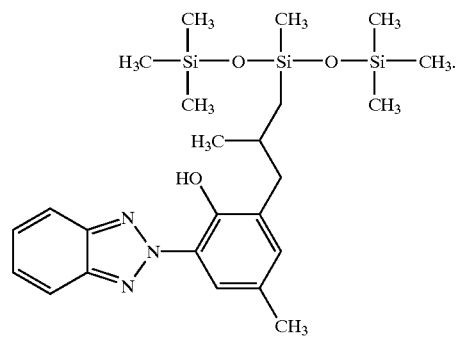

6. The method as defined by claim 1, said keratinous substrate/material comprising human skin, and/or hair.

7. The method as defined by claim 1, wherein the 7-oxo-DHEA compound of formula I is selected from the group consisting of:

3β-O-7-oxo-dehydroepiandrosterone glycinate;
3β-O-7-oxo-dehydroepiandrosterone lysinate;
3β-O-7-oxo-dehydroepiandrosterone α-glutarmate; and
3β-O-7-oxo-dehydroepiandrosterone α-aspartate.

8. The method as defined by claim 1, wherein the 7-oxo-DHEA compound of formula I is 3β-O-7-oxo-dehydroepiandrosterone α-glutamate.

9. The method as defined by claim 1, wherein R' is hydrogen.

10. The method as defined by claim 1, wherein R is an alkylcarbonyl radical wherein the alkyl is a $C_1$–$C_5$ alkyl moiety which is saturated or unsaturated, linear or branched, or cyclic and is subsituted with —COOR' and/or —NR'R'.

* * * * *